(12) United States Patent  
Sasaki et al.

(10) Patent No.: US 7,360,395 B2
(45) Date of Patent: Apr. 22, 2008

(54) GAS SENSOR

(75) Inventors: Takashi Sasaki, Shioya-gun (JP);
Takashi Saito, Shioya-gun (JP);
Akihiro Suzuki, Utsunomiya (JP);
Hidetoshi Oishi, Utsunomiya (JP)

(73) Assignee: Honda Motor Co., Ltd. (JP)

( * ) Notice: Subject to any disclaimer, the term of this patent is extended or adjusted under 35 U.S.C. 154(b) by 72 days.

(21) Appl. No.: 11/386,297

(22) Filed: Mar. 21, 2006

(65) Prior Publication Data

US 2006/0219552 A1 Oct. 5, 2006

(30) Foreign Application Priority Data

Apr. 4, 2005 (JP) ............................ P2005-107806
Jun. 16, 2005 (JP) ............................ P2005-176228

(51) Int. Cl.
*G01N 25/18* (2006.01)
(52) U.S. Cl. ..................................... 73/25.05; 73/25.03
(58) Field of Classification Search ............... 73/25.05, 73/25.03
See application file for complete search history.

(56) References Cited

U.S. PATENT DOCUMENTS

| 3,242,717 | A | * | 3/1966 | Matle et al. .................. 422/90 |
| 5,230,466 | A | * | 7/1993 | Moriya et al. ............ 236/44 A |
| 5,591,635 | A | * | 1/1997 | Young et al. ............ 435/286.1 |
| 6,524,534 | B1 | * | 2/2003 | Tahara et al. ............... 422/105 |
| 7,131,319 | B2 | * | 11/2006 | Ganassi et al. ................ 73/116 |
| 2002/0092779 | A1 | * | 7/2002 | Essalik et al. .............. 205/781 |
| 2002/0118027 | A1 | * | 8/2002 | Routkevitch et al. ....... 324/694 |
| 2003/0005626 | A1 | * | 1/2003 | Yoneda et al. ................. 47/69 |
| 2005/0042141 | A1 | | 2/2005 | Otani et al. |

FOREIGN PATENT DOCUMENTS

| JP | 06-223850 | 8/1994 |
| WO | WO 03/042678 | 5/2003 |

* cited by examiner

*Primary Examiner*—Michael Cygan
(74) *Attorney, Agent, or Firm*—Fish & Richardson P.C.

(57) ABSTRACT

A gas sensor which includes walls delimiting a gas detection chamber, and having an introduction port (or an inlet) through which an observed gas is introduced into the gas detection chamber, a measuring element disposed in the gas detection chamber and measuring concentration of a subject gas contained in the observed gas, and a heater constituting at least a portion of the walls, the portion facing the gas detection chamber.

3 Claims, 10 Drawing Sheets

GAS SENSOR

BACKGROUND OF THE INVENTION

1. Field of the Invention

The present invention relates to a gas sensor such as a catalytic combustion hydrogen sensor which is provided in a fuel-cell vehicle.

Priority is claimed on Japanese Patent Application No. 2005-107806, filed Apr. 4, 2005 and Japanese Patent Application No. 2005-176228, filed Jun. 16, 2005, the contents of which are incorporated herein by reference.

2. Description of Related Art

Conventionally, a known solid polymer membrane fuel cell has a stack including a plurality of cells which are constituted by a solid polymer electrolyte membrane being sandwiched by a fuel electrode and an oxygen electrode (below, simply referred to as the "fuel cell"). Hydrogen is supplied to the fuel electrode as fuel and oxygen is supplied to the oxygen electrode as oxidizing gas. Hydrogen ions generated by a catalytic reaction at the fuel electrode move to the oxygen electrode through the solid polymer electrolyte membrane. Electricity is generated by an electrochemical reaction of the hydrogen ions and oxygen at the oxygen electrode.

In fuel cells including the aforementioned one, a protection device having a hydrogen detector (a gas sensor) provided in an exhaust system of the oxygen electrode of the fuel cell, wherein the protection device stops fuel supply when the gas sensor detects that hydrogen of the fuel electrode has leaked to the oxygen electrode through the solid polymer electrolyte membrane is conventionally known (see, for example, Japanese Unexamined Patent Application, First Publication No. H06-223850).

As the hydrogen detector, a catalytic combustion hydrogen detector having a gas detection element made of a catalytic substance such as platinum and a temperature compensation element is known. When hydrogen contacts the catalytic substance such as platinum, it combusts and heat is generated. The gas detection element reaches high temperature due to the heat and the temperature compensation element, which is at under ambient temperature, is caused to be at relatively low temperature. This hydrogen detector measures a concentration of hydrogen gas in accordance with a difference in electric resistance between the gas detection element and the temperature compensation element generated by the aforementioned process.

In addition, a gas sensor having a tube-shaped case which houses the gas detection element and the temperature compensation element and a tube-shaped heater provided in the case is also known. The inner surface of the heater releases heat and surrounds the gas detection element and the temperature compensation element (PCT International Publication No. WO2003/042678).

Incidentally, in the aforementioned fuel cells, offgas of the fuel cell, especially from the oxygen electrode reaches high humidity because water (hereinbelow, simply referred to as "humidification water") is mixed into the reaction gas (such as hydrogen or oxygen) which is supplied to the fuel cell by a humidification device or the like, in order to maintain the ion-conductivity of the solid polymer electrolyte membrane. Furthermore, water is produced by an electrochemical reaction (so-called "produced water") when the fuel cell operates.

Therefore, in the protection devices disclosed in the aforementioned publications, condensation may occur on the hydrogen detection element provided in a flow path of the offgas from the fuel cell, which has high humidity. In this case, the hydrogen detection element may deteriorate or be damaged. Especially, the water in the offgas readily condenses in the aforementioned solid polymer membrane fuel cell because the fuel cell usually operates at a temperature lower than the one where water becomes vapor and offgas having high humidity is exhausted from the fuel cell. Therefore, when the catalytic combustion hydrogen detector is provided in the exhaust system of the oxygen electrode of the fuel cell, the gas detection element may be broken or decline in sensitivity in a case where topically inhomogeneous temperature of the surface of the gas detection element caused when current is applied to the gas detection element with the humidification water, produced water or the like being deposited on the surface thereof.

When a heater provided for lowering a humidity of the case is provided in the case which houses the gas detection element and the temperature compensation element to solve the aforementioned problem as the above publication discloses, the number of parts of the gas sensor increases and the gas sensor must be large to ensure a detection chamber of a desired size. Furthermore, a notch is made on the wall of the tube-shaped heater along the axial direction to connect two leads for applying current. Therefore, a traverse sectional shape of the heater becomes almost a C-shape and a temperature near the notch becomes relatively low. This may cause inhomogeneous temperature of the surroundings of the gas detection element and the temperature compensation element and may lead to condensation.

SUMMARY OF THE INVENTION

The present invention was made considering the aforementioned circumstances and thus it is an object to provide a gas sensor which is able to prevent damage, degradation, and decline in detection accuracy.

The first aspect of the present invention is a gas sensor including: walls delimiting a gas detection chamber, and having an introduction port through which an observed gas is introduced into the gas detection chamber; a measuring element disposed in the gas detection chamber and measuring concentration of a subject gas contained in the observed gas; and a heater constituting at least a portion of the walls, the portion facing the gas detection chamber.

The heater may be provided facing the gas detection chamber. In this case, relative humidity can be lowered by the heater even when an observed gas of high relative humidity brings water into the gas detection chamber.

The gas sensor may further include a first dehumidifier absorbing water in a reversible manner, and disposed on a portion of the walls that is located opposite the introduction port with respect to the measuring element. In this case, the produced water can be absorbed by the first dehumidifier. Therefore, decline in accuracy of detection of the subject gas, and damage or degradation caused when current is applied to the measuring element with water being deposited on the surface thereof can be prevented.

The heater may include a first heater which is tube-shaped and a second heater which is ring-shaped, and the first dehumidifier be provided to be sandwiched between the first heater and the second heater. In this case, the first dehumidifier can be maintained to absorb a desired amount of water which is deposited at a position where condensation is likely to occur and develop.

The gas sensor may further including a second dehumidifier absorbing water in a reversible manner, and disposed between the measuring element and the introduction port. In this case, a relative humidity of the observed gas to which the measuring element is exposed can be lowered and condensation on the surface of the measuring element can be prevented.

The heater may be provided to be sandwiched between the first dehumidifier and the second dehumidifier. In this case, the first dehumidifier and the second dehumidifier can be heated and dried (that is, to release water) by the heater, and be maintained to absorb a desired amount of water.

The heater may constitute the entirety of the walls. In this case, a temperature and a humidity of the gas detection chamber and a temperature of the surface of the measuring element can be maintained uniform. At the same time, a desired temperature and a desired humidity can be easily set. Therefore, condensation due to inhomogeneous temperature or humidity in the gas detection chamber can be prevented.

In addition, since there is no need to provide an extra heater in the gas detection chamber, a detection space of the gas detection chamber can be enlarged without an enlargement of the gas sensor itself. This leads to prevention of drastic changes in temperature and humidity of the detection space and the temperature of ambient gas and the measuring element in the detection space rapidly lowering below dew point. In addition, the accuracy of detection of the observed gas can be improved because the amount of the observed gas introduced to the gas detection chamber can be increased.

The gas sensor may further include a third dehumidifier absorbing water in a reversible manner, and being disposed on the heater. In this case, a temperature of the third dehumidifier can be directly controlled. Therefore, the third dehumidifier can be secured to absorb a desired amount of water by being heated and dried (that is, to release water) by the heater.

DETAILED DESCRIPTION OF THE INVENTION

Figure 1:
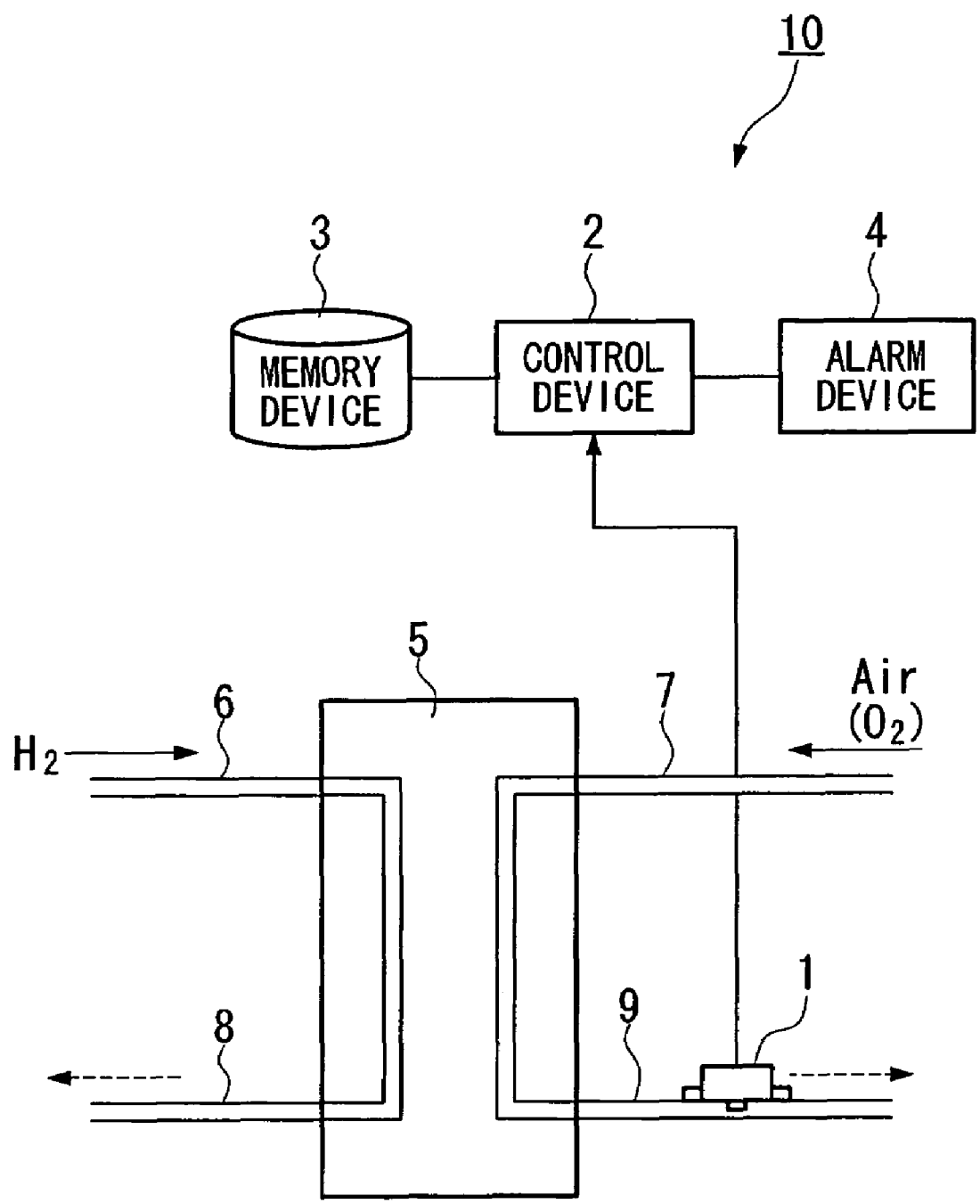
FIG. 1 is a block diagram of a fuel cell system having a gas sensor of a first embodiment of the present invention.

A gas sensor of a first embodiment of the present invention is described hereinbelow, with reference to the drawings.

A gas sensor 1 of this embodiment is, for example, a hydrogen sensor which measures hydrogen. The gas sensor 1 is provided in a fuel cell system 10 including a control device 2, a memory device 3, an alarm device 4, a fuel cell 5 which drives a vehicle, and pipes 6, 7, 8 and 9 (inlet pipes 6 and 7, outlet pipes 8 and 9) which are connected to the fuel cell 5 and supply reaction gas thereto. The gas sensor 1 is provided above (in terms of gravity) the outlet pipe 9 extending from the oxygen electrode, to monitor whether or not hydrogen is exhausted from the outlet pipe 9.

The control device 2 is connected to the gas sensor 1 provided on the outlet pipe 9 and determines whether or not there is an abnormality in accordance with, for example, a comparison result of a detection signal output from the gas sensor 1 with a predetermined threshold value stored in the memory device 3. When the control device 2 determines that there is an abnormality, it makes the alarm device 4 outputs an alarm. The memory device 3 stores a map of predetermined threshold values of the detection value of the gas sensor 1 in accordance with operational conditions of the fuel cell 5 such as a pressure difference between electrodes and operation pressure or the like.

The fuel cell 5 is provided in a vehicle such as an electric vehicle as a drive source. The fuel cell 5 is constituted by a plurality of cells (not illustrated), each cell consisting of an electrolyte electrode structure, in which a solid polymer electrolyte membrane is held between a fuel electrode and an oxygen electrode, and sandwiched by separators.

When fuel gas such as hydrogen is supplied from the inlet pipe 6 to the fuel electrode, the hydrogen is ionized at a catalyst electrode of the fuel electrode. The hydrogen ions move to the oxygen electrode through the solid polymer electrolyte membrane which is properly humidified. Generated electrons are taken out to an outer circuit and used as direct current energy. Since oxidizing gas such as oxygen or air is supplied to the oxygen electrode via the inlet pipe 7, water is generated at the oxygen electrode as a result of a reaction of hydrogen ions, electrons, and oxygen. Offgas remaining after the reaction is exhausted from the outlet pipes 8 and 9 from the fuel electrode and the oxygen electrode respectively.

Since the gas sensor 1 is provided on the upper side of the outlet pipe 9 from the oxygen electrode, generated water is exhausted on the bottom even when the offgas of the oxygen electrode is cooled and condensation occurs.

Figure 2:
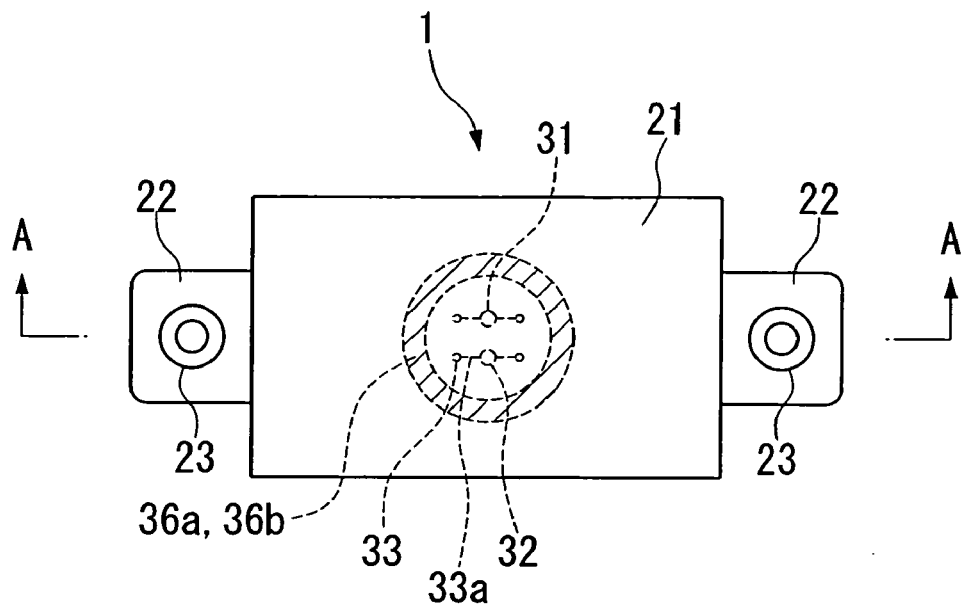
FIG. 2 is a sectional view of the gas sensor shown in FIG. 1.
Figure 3:
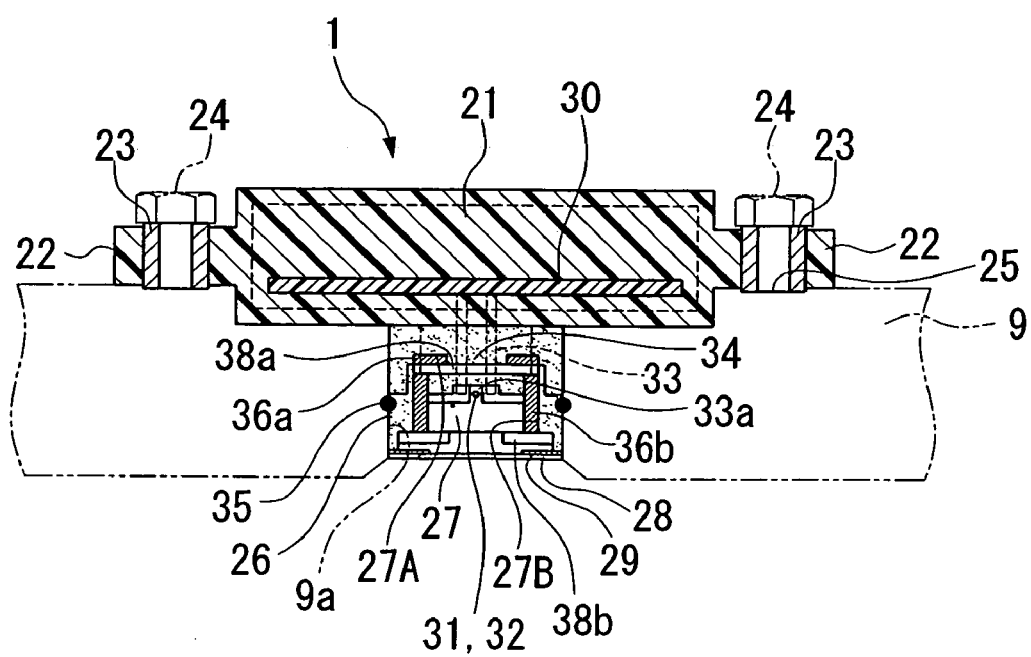
FIG. 3 is a schematic sectional view along line A-A of FIG. 2.
Figure 4:
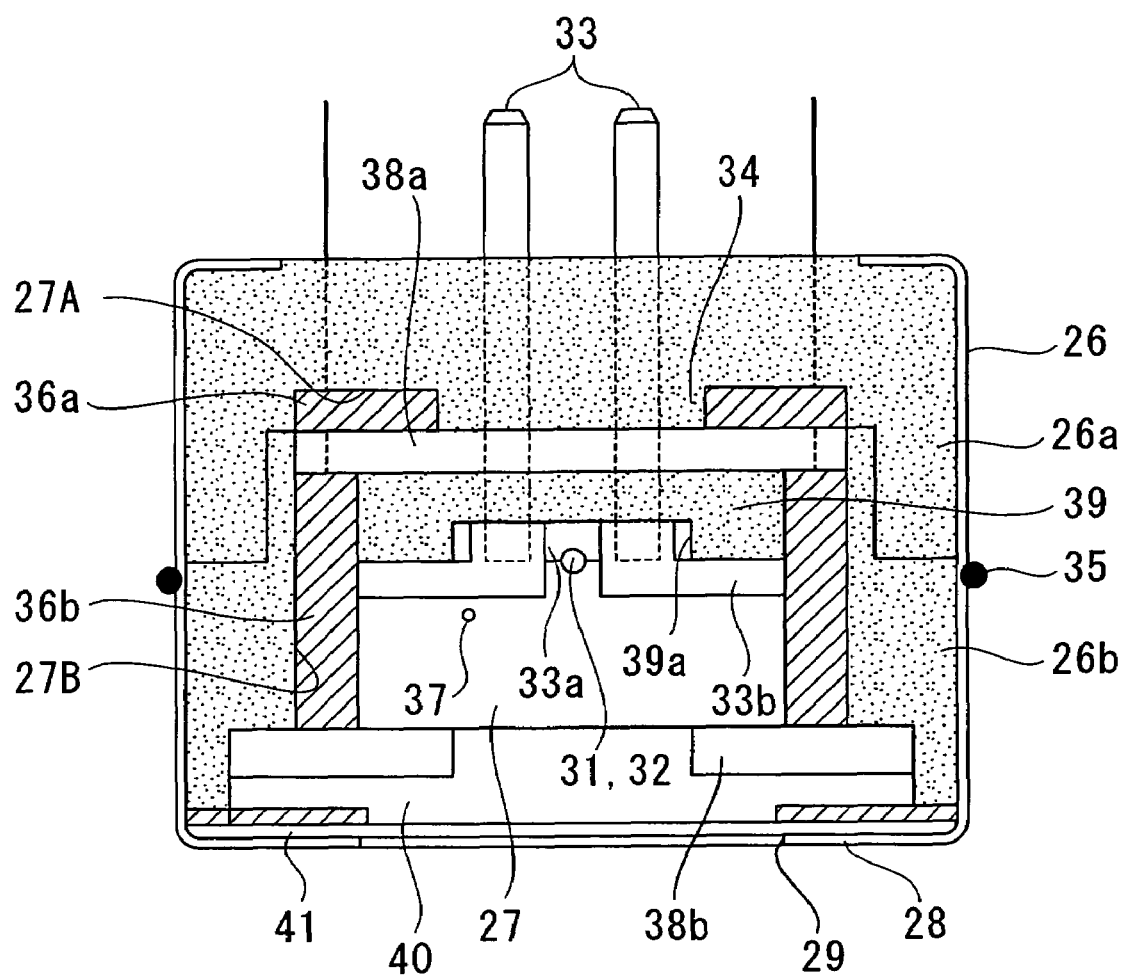
FIG. 4 is a detailed sectional view of the gas detection chamber shown in FIG. 3.

The gas sensor 1 has a rectangular case 21 extending along the outlet pipe 9, that is, in the horizontal direction, for example, shown in FIGS. 2 to 4. The case 21 is made of, for example, polyphenylene sulfide and has flange portions 22 at both ends in the longitudinal direction. Collars 23 are attached to the flange portions 22. The flange portions 22 are adapted to be clinched and fixed on a fixing base 25 provided on the outlet pipe 9 of the oxygen electrode by inserting bolts 24 into the collars 23 as shown in FIG. 3.

A tube portion 26 is provided at an end in the thickness direction of the case 21 as shown in FIGS. 3 and 4. The tube portion 26 is constituted for example of a tube-shaped tube end portion 26a having a bottom and a tube-shaped tube tip portion 26b, being connected along the same axis. The inner space of the tube portion 26 is constituted as a gas detection chamber 27. A flange portion 28 is provided on the inner surface of the tube portion 26 toward the inside thereof and a space inside the flange portion 28 is constituted to open as a gas introduction portion 29.

A sealing member 35 is attached to the outer surface of the tube portion 26 and assures airtightness by adhering to the inner wall that defines a hole 9a of the outlet pipe 9.

A circuit board 30 sealed in a resin is provided in the case 21 and a gas detection element 31 and a temperature compensation element 32 provided in the gas detection chamber 27 are connected to the circuit board 30 by a plurality of (for example, four) stays 33 for power distribution and a lead 33a which are connected to the circuit board 30.

In the gas detection chamber 27, a base portion 34 of the tube end portion 26a, a first heater 36a, a second heater 36b, a sensor 37 which measures a temperature and a humidity of the gas detection chamber 27, a first dehumidifier 38a, a second dehumidifier 38b, a structure member 39, a sintered filter 40, and a water-repellent filter are disposed with the gas detection element 31 and the temperature compensation element 32.

The base portion 34, the first dehumidifier 38a, and the structure member 39 are disposed from the bottom surface 27A of the gas detection chamber 27 to the tip portion of the gas sensor 1 along the thickness direction thereof in series. The four stays 33 for power distribution penetrate the disk-shaped base portion 34, the disc-shaped first dehumidifier 38a, and the disc-shaped structure member 39, and are fixed by the base portion 34.

Appropriate covers for preventing corrosion are provided on the surfaces of the stays 33. The structure member 39 is made of polyphenylene sulfide or phenol resin and has a recess portion 39a provided at the tip portion of the structure member 39 toward the base portion thereof. An annular stay cover 33b is disposed to entirely cover an exposed portion of the four stays 33 which are exposed in the recess portion 39a.

A set of the gas detection element 31 and the temperature compensation element 32 is disposed by the lead 33a connected to the stays 33 at a predetermined distance, in a space which is delimited by the recess portion 39a and the stay cover 33b and communicates with the gas detection chamber 27, and a predetermined distance apart from the base portion 34 in the thickness direction of the gas sensor 1.

As shown in FIG. 4, the first heater 36a made of, for example, an annular ceramic heater is disposed on the bottom surface 27A of the gas detection chamber 27 and covers at least a portion inside the gas detection chamber 27. The inner wall of the first heater 36a is provided to face the outer portion of the base portion 34 which is disposed on the bottom surface 27A of the gas detection chamber 27.

The second heater 36b made of, for example, a tube-shaped ceramic heater is disposed on the inner wall 27B of the gas detection chamber 27 and covers at least a portion inside the gas detection chamber 27. The outer wall of the second heater 36b is provided to cover the inner wall 27B of the gas detection chamber 27. The inner wall of the second heater 36b is provided to face the outer wall of the structure member 39 and the stay cover 33b.

One side of the first heater 36a abuts the bottom surface of the gas detection chamber 27. A first dehumidifier 38a is sandwiched by the opposite side of the first heater 36a and one end of the second heater 36b. An annular second dehumidifier 38b is provided to abut the opposite side of the second heater 36b.

The first heater 36a and the second heater 36b are ceramic heaters, for example, ceramic heaters having conductive ceramics as an exothermic body or ceramic heaters having a resistance body made of a metal provided in a nonconductive ceramics, These heaters are adapted to heat the inside of the gas detection chamber 27, the gas detection element 31, the temperature compensation element 32, the first dehumidifier 38a, and the second dehumidifier 38b when powered by the circuit board 30 which is connected to the first heater 36a and the second heater 36b in a parallel manner. For example, in this embodiment, the first heater 36a heats the first dehumidifier 38a, and the second heater 36b heats the first dehumidifier 38a and the second dehumidifier 38b.

The second dehumidifier 38b, an annular sintered filter 40, and a water-repellent filter 41 which covers the gas introduction portion 29 are disposed between the opposite side of the second heater 36b and the gas introduction portion 29, from a base portion to the tip portion of the gas sensor 1 along the thickness direction thereof in series.

The first dehumidifier 38a and the second dehumidifier 38b are made of materials which absorb water in accordance with ambient humidity such as silica gel, zeolite, activated charcoal, activated alumina, water-absorbing polymer, or oxidized zirconium. These dehumidifiers can release water which they absorb into the ambient gas as vapor when heated by the first heater 36a and the second heater 36b and are constituted to absorb water in a reversible manner.

The sintered filter 40 and the water-repellent filter 41 are adapted to be permeable to the observed gas and the gas detection chamber 27 is adapted for the offgas which flows through the outlet pipe 9 to enter the gas detection chamber 27 through at least the sintered filter 40 and the water-repellent filter 41.

Figure 5:
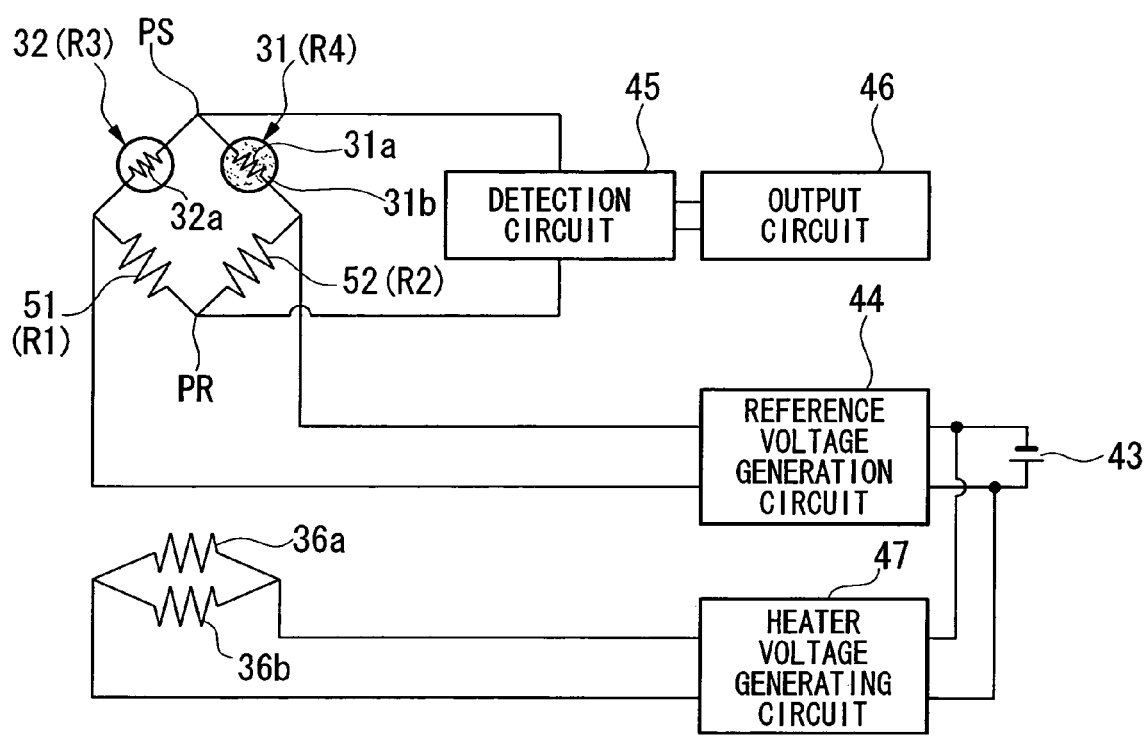
FIG. 5 is a diagram showing a circuit of the gas sensor shown in FIG. 1.
Figure 6:
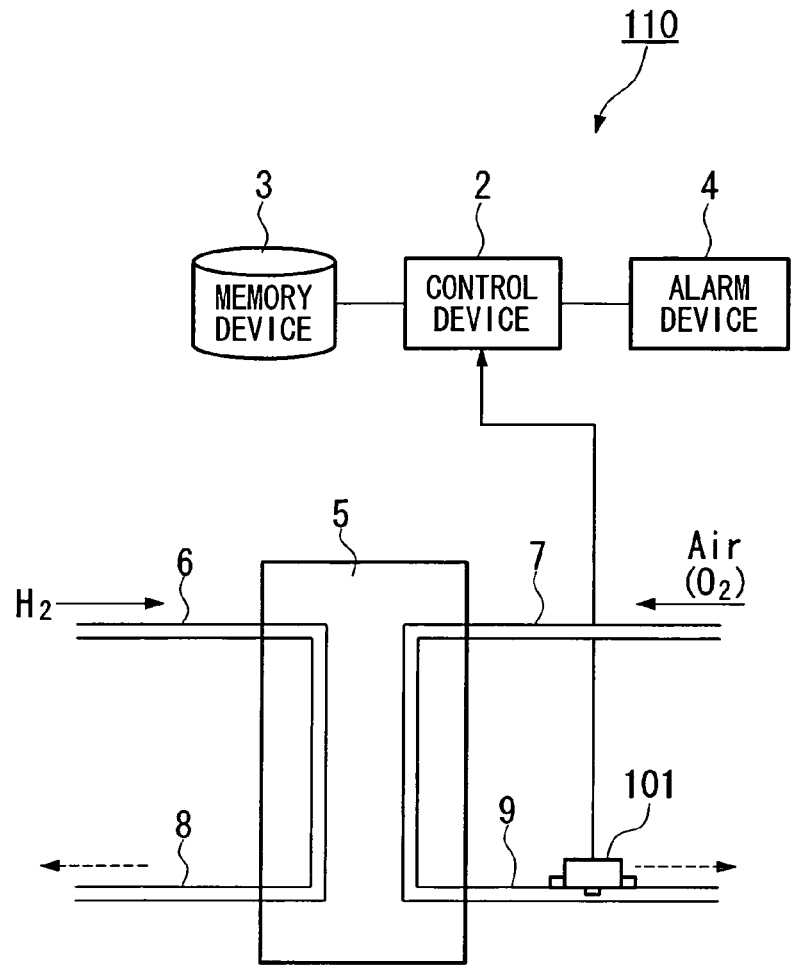
FIG. 6 is a block diagram of a fuel cell system having a gas sensor of a second embodiment of the present invention.

As shown in FIG. 5, the gas detection element 31 is a known element and is made of a coil 31a made of metals such as platinum. The gas detection element 31 is constituted of the coil 31a, the surface thereof being covered with catalyst carrier such as alumina, which supports a catalyst 31b made of a noble metal active for the subject gas of hydrogen.

The temperature compensation element 32 is made inactive to the subject gas and is constituted of a coil 32a, the coil 32a itself being identical to that of the gas detection element 31 and the surface thereof being covered with catalyst carrier such as alumina.

The gas sensor 1 can measure a concentration of hydrogen by measuring a difference in electric resistance between the gas detection element 31, when it reaches high temperature due to the reaction heat generated when the subject gas of hydrogen contacts the catalyst 31b of the gas detection element, and the temperature compensation element 32 which is at a lower temperature than the gas detection element 31 because of not reacting with the subject gas, while canceling a change in electric resistance due to a change in ambient temperature.

As shown in FIG. 5, a bridge circuit is constituted by a branch in which the gas detection element 31 (resistance value: R4) being connected to the temperature compensation element 32 (resistance value: R3) in series and a branch in which a fixed resistor 51 (resistance value: R1) being connected to a fixed resistor 52 (resistance value: R2) in series being connected to a reference voltage generation circuit 44 which applies a predetermined voltage based on the voltage supplied from an outer power supply 43 in parallel.

In this bridge circuit, a detection circuit 45 is connected between a connecting point PS of the gas detection element 31 and the temperature compensation element 32, and a connecting point PR of the fixed resistor 51 and the fixed resistor 52. The detection circuit 45 measures a voltage between the connecting points PS and PR. An output circuit 46 is connected to the detection circuit 45.

When the subject gas of hydrogen is not present in the observed gas introduced to the gas detection chamber 27, the bridge circuit is in a balanced state where an expression R1×R4=R2×R3 is true and the output of the detection circuit 45 becomes zero. On the other hand, when hydrogen is present it combusts at the catalyst 31b of the gas detection element 31. As a result, the temperature of the coil 31a becomes higher and the resistance value R4 increases. Since hydrogen does not combust at the temperature compensation element 32, the resistance value R3 does not change. Thereby, the balance of the bridge circuit is lost and a voltage which increases in accordance with the concentration of hydrogen is applied to the detection circuit 45. The voltage value is output from the detection circuit 45 to the output circuit 46 and the output circuit 46 outputs the voltage value to the control device 2. The concentration of hydrogen is computed in the control device 2 based on the map thereof which is predetermined in accordance with the voltage value.

A heater voltage generating circuit 47 which applies suitable voltage to the first heater 36a and the second heater 36b is connected to the outer power supply 43 to which the reference voltage generation circuit 44 is connected. The first heater 36a and the second heater 36b are connected to the heater voltage generating circuit 47 in parallel to each other.

The control device 2 is connected to the sensor 37, the first heater 36a, and the second heater 36b in the gas detection chamber 27, and controls operational conditions of the gas detection element 31, the temperature compensation element 32, the first heater 36a, and the second heater 36b, for example, timing of start and stop of power distribution and amount thereof, in accordance with conditions of temperature and humidity of the ambient gas in the gas detection chamber 27 output from the sensor 37, conditions on loading and operation of the fuel cell 5 or the like. At this time, the control device 2 controls the amount of power distribution to the first heater 36a and the second heater 36b by feedback control in accordance with the current values distributed to the first heater 36a and the second heater 36b and chopper control (that is, switching on and off of the power distribution) based on on/off operations of a switching element, or the like.

For example, the control device 2 controls the power distribution to the first heater 36a and the second heater 36b based on the temperature measured by the sensor 37 so that the temperature of the gas detection chamber 27 is within a predetermined range which is at least more than a dew-point temperature. The control device 2 also controls the timing of start and stop of power distribution and amounts thereof to the first heater 36a and the second heater 36b so that the relative humidity of the gas detection chamber 27 which is measured by the sensor 37 becomes identical to an index value listed in the predetermined relative humidity map in accordance with the temperature of the gas detection chamber 27.

Furthermore, the control device 2 controls amounts of power distribution to the first heater 36a and the second heater 36b in accordance with various parameters such as operating conditions of the fuel cell 5 (including start and stop), conditions of the loading of the fuel cell 5 during operation, such as a command to generate electricity sent to the fuel cell 5 (FC output command value), a current value of the fuel cell 5 measured by an output current sensor (not illustrated), and power generating conditions of the fuel cell 5 calculated based on a flow volume of the air supplied from an air compressor (not illustrated) to the fuel cell 5 measured by a flow volume sensor (not illustrated).

When the loading of the fuel cell 5 becomes higher and there is a risk of the temperature inside the detection chamber 27 of the gas sensor 1 lowering due to an increase of the offgas which flows through the outlet pipe 9 of the oxygen electrode and cools the gas sensor 1, or of the relative humidity inside the gas detection chamber 27 increasing due to an increase of the produced water which is generated in the fuel cell 5 and included in the offgas, the control device 2 prevents condensation in the gas detection chamber 27 by raising the temperature inside the gas detection chamber 27. On the other hand, the control device 2 reduces energy consumption by lowering the amounts of power distribution to the first heater 36a and the second heater 36b when the loading of the fuel cell 5 becomes lower.

In addition, when a purge is conducted to drain water left in the fuel cell system due to an increase of the offgas flowing through the outlet pipes 8 and 9 when stopping operation of the fuel cell 5, the control device 2 increases the volume of the saturated water vapor of the ambient gas in the gas detection chamber 27 by raising the temperature of the gas detection chamber 27 by increasing power distribution to the first heater 36a and the second heater 36b. Thereby, condensation in the gas detection chamber is prevented.

The control device 2 starts power distribution to the gas detection element 31, the temperature compensation element 32, the first heater 36a, and the second heater 36b before starting offgas flow in the outlet pipe 9 of the oxygen electrode when starting the fuel cell 5, and stops power distribution to the gas detection element 31, the temperature compensation element 32, the first heater 36a, and the second heater 36b after stopping offgas flow in the outlet pipe 9 of the oxygen electrode when stopping the fuel cell 5.

Functions of the gas sensor 1 of the aforementioned embodiment are described.

The first dehumidifier 38a and the second dehumidifier 38b provided in the gas detection chamber 27 absorb and release water in accordance with the humidity of the ambient gas in the gas detection chamber 27. For example, relative humidity in the gas detection chamber 27 decreases when power is distributed to the first heater 36a and the second heater 36b during operation of the gas sensor 1, due to the rise of the temperature inside the gas detection chamber 27. The first dehumidifier 38a and the second dehumidifier 38b release water, and thus, more water can be absorbed therein. When the power distribution to the first heater 36a and the second heater 36b is stopped after offgas flow in the outlet pipe 9 is stopped when the fuel cell 5 is stopped, the relative humidity in the gas detection chamber 27 increases due to the decline of the temperature inside the gas detection chamber 27. At this time, the first dehumidifier 38a and the second dehumidifier 38b absorb water including water vapor in the ambient gas in the gas detection chamber 27 in accordance with their capacities. Thereby conditions in which condensation occurs such as the relative humidity in the gas detection chamber 27 becoming 100% and the temperature of the gas detection chamber becoming equal to or less than the dew-point temperature can be prevented from occurring. In addition, even if condensation occurs when a temperature of a portion of the gas detection chamber 27 becomes equal to or less than the dew-point temperature, the water generated by condensation can be absorbed by the first dehumidifier 38a and the second dehumidifier 38b.

In particular, in the gas detection chamber 27, the region between the base portion 34 and the gas detection element 31 and the temperature compensation element 32 is likely to be the situations of condensation and generated condensation is likely to remain. The first dehumidifier 38a provided opposite of the introduction portion 29 with respect to the gas detection element 31 and the temperature compensation element 32 is dried (that is, releases water) by the first heater 36a and the second heater 36b to absorb a desired amount of water surely. Thereby condensation at an upper region of the gas detection element 31 and the temperature compensation element 32 or the like can be prevented.

The second dehumidifier 38b provided nearer the gas introduction portion 29 in relation to the second heater 36b and between the gas detection element 31 and the temperature compensation element 32, and the gas introduction portion 29 can decrease the relative humidity of the ambient gas, to which the gas detection element 31 and the temperature compensation element 32 are exposed, and prevent condensation on the surface of the gas detection element 31 and the temperature compensation element 32.

Since the second heater 36b is provided to cover the inner wall 27B of the gas detection chamber 27, condensation on the inner wall 27B near the tube portion where condensation is likely to occur due to being made of a metal of relatively high heat conductivity can be prevented.

As described above, in the gas sensor 1 of the present embodiment, condensation in the gas detection chamber 27 can be prevented by the first dehumidifier 38a and the second dehumidifier 38b which absorb water included in the ambient gas in the gas detection chamber 27, decrease the relative humidity thereof, and prevent the temperatures of the ambient gas and the surfaces of the gas detection element 31 and the temperature compensation element 32 from declining to be equal to or less than the dew-point temperature, even when the temperatures of the ambient gas and the surfaces of the gas detection element 31 and the temperature compensation element 32 decline when the first heater 36a and the second heater 36b which maintain the temperature and humidity of the ambient gas and the temperatures of the surface of the gas detection element 31 and the temperature compensation element 32 are stopped.

In addition, even when condensation occurs due to a local decrease in temperature or the like because of a stoppage of the first heater 36a and the second heater 36b, water generated by condensation can be absorbed by the first dehumidifier 38a and the second dehumidifier 38b. Thereby a condition where condensation on the gas sensor 1 remains when restarting can be prevented and the relative humidity in the gas detection chamber 27 can be decreased in advance for the next operation of the gas sensor 1.

The relative humidity of the gas detection chamber 27 can be decreased by the second heater 36b covering the inner wall 27B of the gas detection chamber 27 even when water included in the offgas of high relative humidity or the like entered the gas detection chamber 27.

Since the first dehumidifier 38a is provided in the region opposite to the introduction portion 29 with respect to the gas detection element 31 and the temperature compensation element 32 on which condensation is likely to form and remain, water generated by condensation can be absorbed. Thereby deterioration and degradation of the gas detection element 31 and the temperature compensation element 32 when they are powered with condensation remaining can be prevented.

Furthermore, since the outer power supply 43 supplies power to a detection portion including the gas detection element 31, the temperature compensation element 32, the fixed resistors 51 and 52, the first heater 36a, and the second heater 36b, the structure of the circuit can be simplified.

Although the gas sensor 1 is a hydrogen sensor in the aforementioned embodiment, the gas sensor of the present invention is not limited thereto. The gas sensor may be one which measures other gases such as a combustible gas of carbon monoxide and methane or the like.

In addition, although the gas sensor 1 is a catalytic combustion sensor in the aforementioned embodiment, the gas sensor of the present invention is not limited thereto. The gas sensor may be of another type such as a semiconductor type.

Furthermore, although the bridge circuit to which the gas detection element 31 and the temperature compensation element 32 are connected is provided in the gas sensor 1 of the aforementioned embodiment, the circuit is not limited thereto. The circuit may be of another type such as a series circuit and values of voltage or current between predetermined connecting points may be output to the control device 2 as parameters related to the resistance value R4 of the gas detection element 31.

A gas sensor according to the second embodiment of the present invention is described hereinbelow with reference to the drawings. A gas sensor 101 of the present embodiment is, for example, a hydrogen sensor which measures hydrogen. The gas sensor 101 is provided in a fuel cell system 110 including a control device 2, a memory device 3, an alarm device 4, a fuel cell 5 which drives a vehicle, and pipes 6, 7, 8 and 9 (inlet pipes 6 and 7, outlet pipes 8 and 9) which are connected to the fuel cell 5 and supply reaction gas thereto. The gas sensor 101 is provided above (in terms of gravity) the outlet pipe 9 extending from the oxygen electrode, to monitor whether or not hydrogen is exhausted from the outlet pipe 9. Since the control device 2, the memory device 3, the alarm device 4, the fuel cell 5, and the pipes 6, 7, 8, and 9 are identical to those of the first embodiment, redundant descriptions are omitted.

Figure 7:
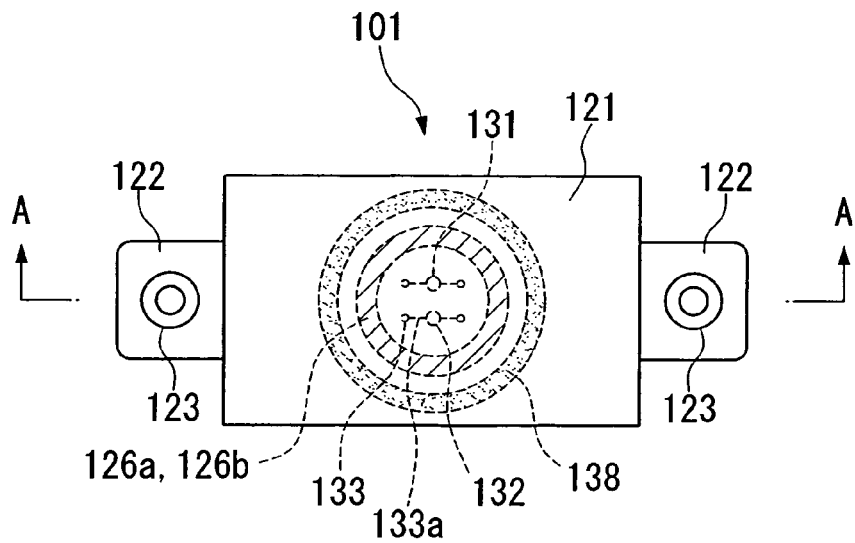
FIG. 7 is a sectional view of the gas sensor shown in FIG. 6.
Figure 8:
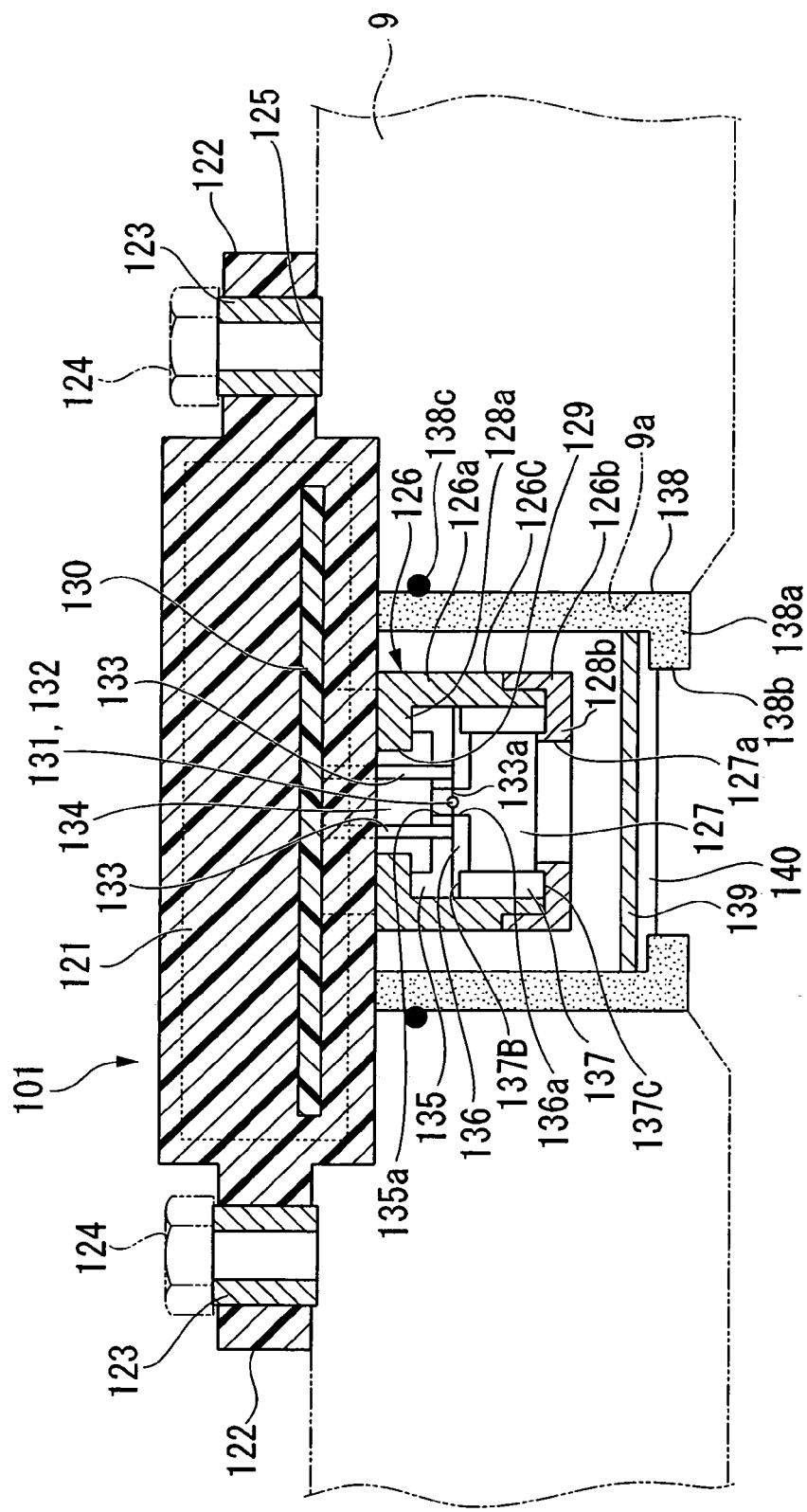
FIG. 8 is a schematic sectional view along line A-A of FIG. 7.
Figure 9:
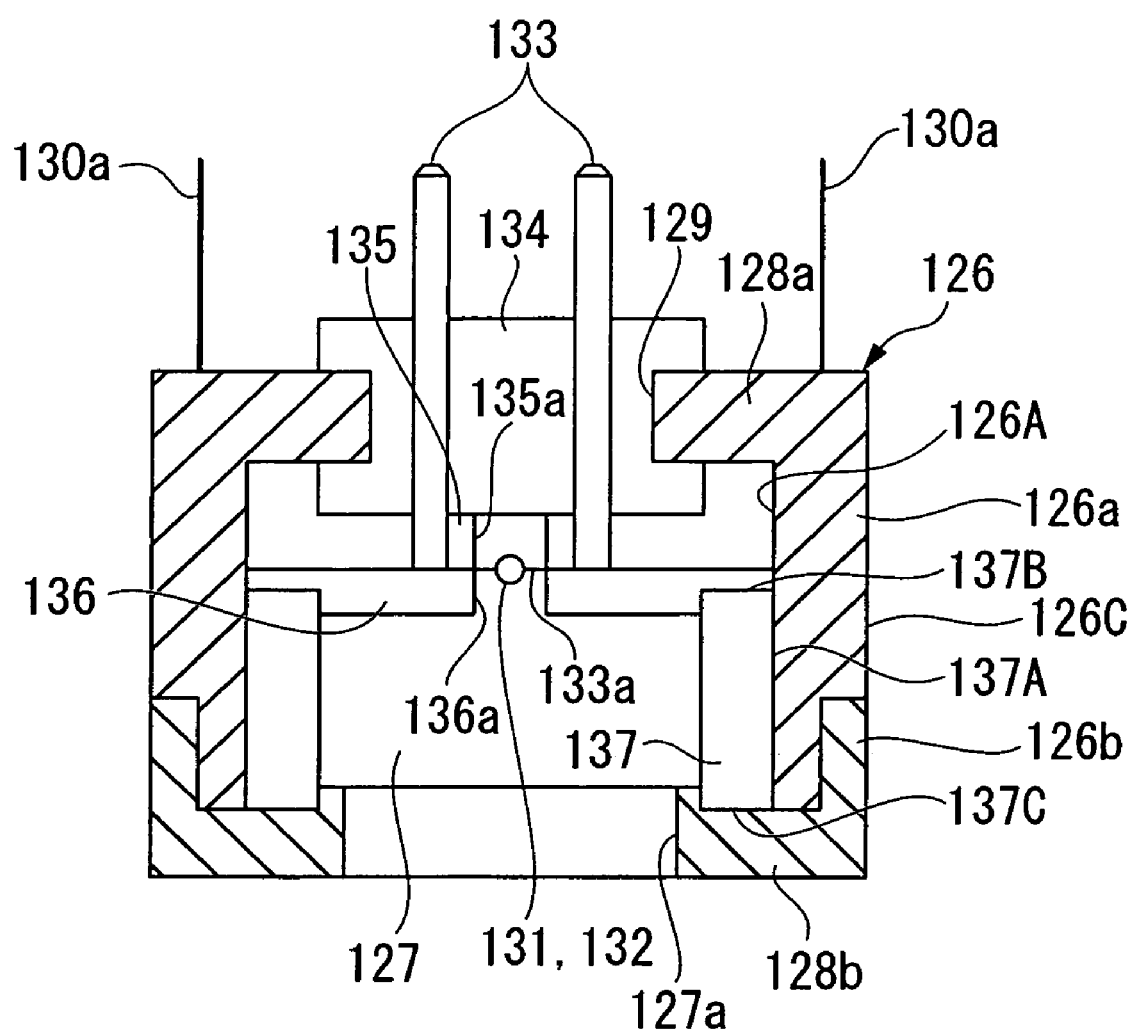
FIG. 9 is a detailed sectional view of the gas detection chamber shown in FIG. 8.

The gas sensor 101 has a rectangular case 121 extending along the outlet pipe 9, that is, in the horizontal direction, for example, shown in FIGS. 7 to 9. The case 121 is made of, for example, polyphenylene sulfide and has flange portions 122 at both ends in the longitudinal direction. Collars 123 are attached to the flange portions 122. The flange portions 122 are adapted to be clinched and fixed on a fixing base 125 provided on the outlet pipe 9 of the oxygen electrode by inserting bolts 124 in the collars 123 as shown in FIG. 8.

A tube portion 126 made of ceramic is provided at an end in the thickness direction of the case 121 as shown in FIGS. 8 and 9. The tube portion 126 is constituted, for example, of a tube-shaped tube main portion 126a and a tube-shaped tube tip portion 126b, being connected along the same axis in the thickness direction of the gas sensor 101.

The inner space of the tube portion 126 is constituted as a gas detection chamber 127. A base flange portion 128a made of ceramic is provided on the inner surface of the tube main portion 126a in an integrated manner toward the inside thereof and the inner wall of the base flange portion 128a is constituted to open as a stay providing portion 129.

A tip flange portion 128b made of ceramic is provided on the inner surface of the tube tip portion 126b in an integrated manner toward the inside thereof and an inner wall of the tip flange portion 128b is constituted to open as a gas introduction portion 127a.

Among the components of the tube portion 126 made of ceramics, the tube base portion 126a and the base flange portion 128a formed as a single member is a ceramic heater powered from a circuit board 130 in the case 121 via a wiring 130a. This ceramic heater is, for example, one having conductive ceramic as an exothermic body or one having a resistance body made of a metal provided in a nonconductive ceramic.

In other words, the gas detection chamber 127 is defined by the tube main portion 126a which is a ceramic heater and the inner wall of the gas detection chamber 127 is formed by the inner surface 126A of the tube main portion 126a.

The circuit board 130 is sealed in a resin and is provided in the case 121, and a gas detection element 131 and a temperature compensation element 132 provided in the gas detection chamber 127 are connected to the circuit board 130 by a plurality of (for example, four) stays 133 for power distribution and a lead 133a which are connected to the circuit board 130.

The four stays 133 for power distribution penetrate a waterproof plug 134 which seals the stay providing portion 129 of the tube main portion 126a and an annular base portion 135 which is provided in the gas detection chamber 127, and are fixed, for example, by the base portion 135.

The waterproof plug 134 is, for example, made of rubber and adheres to the inner surface of the stay providing portion 129 and the base flange portion 128a. The water proof plug 134 also adheres to the surfaces of the stays 133 which penetrate the waterproof plug 134 and assures airtightness and waterproof of the circuit board 130.

The annular base portion 135 is provided at the base of the gas detection chamber 127 and the outer surface of the base portion 135 contacts the inner surface 126A of the tube main portion 126a which constitutes the inner wall of the gas detection chamber 127.

Appropriate covers for preventing corrosion are provided on the surfaces of the stays 133. An annular stay cover 136 for preventing degradation due to such as corrosion is disposed to entirely cover an exposed portion of the four stays 133 which penetrate the waterproof plug 134 and the base portion 135 and are exposed in the gas detection chamber 127, and connection portions of the lead 133a which are connected to a set of the gas detection element 131 and the temperature compensation element 132 and the stays 133.

A set of the gas detection element 131 and the temperature compensation element 132 is disposed by the lead 133a connected to the stays 133 at a predetermined distance, in a space which is delimited by a hole 135a of the annular base portion 135 and a hole 136a of the stay cover 136 and communicates with the gas detection chamber 127, and a predetermined distance apart from the base portion 135 in the thickness direction of the gas sensor 101.

A dehumidifier 137 which is, for example, tube-shaped and absorbs in a reversible manner is provided and the outer surface 137A of the dehumidifier 137 contacts the inner surface 126A of the tube main portion 126a which constitutes the inner wall of the gas detection chamber 127. The dehumidifier 137 is provided to be sandwiched by the stay cover 136 and the tip flange portion 128b, the base end 137B of the dehumidifier 137 contacts the stay cover 136, and the tip end 137C of the dehumidifier 137 contacts the tip flange 128b.

The dehumidifier 137 is made of materials which absorb water in accordance with ambient humidity such as silica gel, zeolite, activated charcoal, activated alumina, water-absorbing polymer, and oxidized zirconium. The dehumidifier 137 can release water which it absorbed in the ambient gas as vapor when heated by the tube main portion 126a, which is a ceramic heater and is constituted to absorb water in a reversible manner.

A tube-shaped outer case 138 which houses the tube portion 126 inside is provided along the thickness direction of the gas sensor 101 at a position a predetermined distance apart from an outer surface 126C of the tube portion 126, for example as shown in FIG. 8. A flange portion 138a is provided on the inner surface of the outer case 138 in an integrated manner toward the inside thereof and the inner portion of the flange portion 138a is constituted to open as a gas introduction port 138b.

A disc-shaped sintered filter 139 and a disc-shaped water-repellent filter 140 are disposed inside the tip of the outer case 138 from a base portion to the tip portion of the gas sensor 101 along the thickness direction thereof in series, and the water-repellent filter 140 covers the gas introduction portion 138b.

The sintered filter 139 and the water-repellent filter 140 are adapted to be permeable to the observed gas and the gas detection chamber 127 is adapted for the offgas which flows through the outlet pipe 9 to enter the outer case 138 and the gas detection chamber 127 through at least the sintered filter 139 and the water repellent filter 140.

Condensation around the gas detection element 131 and the temperature compensation element 132 can be prevented by a gap between the sintered filter 139 and the base flange portion 128a.

A sealing member 138c is attached on the outer surface of the outer case 138 and assures airtightness by adhering to the inner wall of a hall 9a of the outlet pipe 9.

Figure 10:
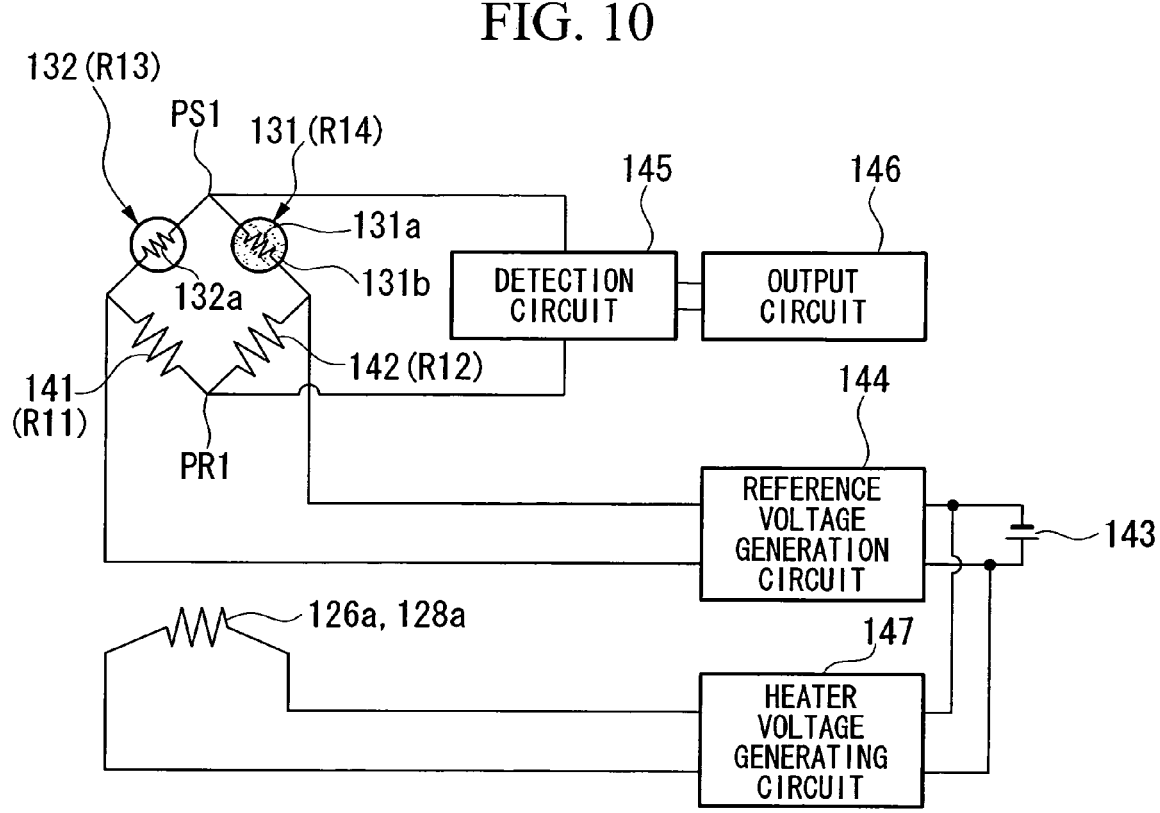
FIG. 10 is a diagram showing a circuit of the gas sensor shown in FIG. 6.

As shown in FIG. 10, the gas detection element 131 is a known element and is made of a coil 131a made of metals such as platinum. The gas detection element 131 is constituted of the coil 131a, the surface thereof being covered with catalyst carrier such as alumina, which supports a catalyst 131b made of a noble metal active for the subject gas of hydrogen.

The temperature compensation element 132 is made inactive to the subject gas and is constituted of a coil 132a, the coil 132a itself being identical to that of the gas detection element 131 and the surface thereof being covered with catalyst carrier such as alumina.

The gas sensor 101 can measure a concentration of hydrogen by measuring a difference in electric resistance between the gas detection element 131, when it reaches high temperature due to the reaction heat generated when the subject gas of hydrogen contacts the catalyst 131b of the gas detection element, and the temperature compensation element 132, which is at a lower temperature than the gas detection element because of not reacting with the subject gas, while canceling a change in electric resistance due to a change in ambient temperature.

As shown in FIG. 10, a bridge circuit is constituted by a branch in which the gas detection element 131 (resistance value: R14) being connected to the temperature compensation element 132 (resistance value: R13) in series and a branch in which a fixed resistor 151 (resistance value: R11) being connected to a fixed resistor 152 (resistance value: R12) in series being connected to a reference voltage generation circuit 144 which applies a predetermined voltage based on the voltage supplied from an outer power supply 143 in parallel.

In this bridge circuit, a detection circuit 145 is connected between a connecting point PS1 of the gas detection element 131 and the temperature compensation element 132, and a connecting point PR1 of the fixed resistor 151 and the fixed resistor 152. The detection circuit 145 measures a voltage between the connecting points PS1 and PR1. An output circuit 146 is connected to the detection circuit 145.

When the subject gas of hydrogen is not present in the observed gas introduced to the gas detection chamber 127, the bridge circuit is in a balanced state where an expression R11×R14=R12×R13 is true and the output of the detection circuit 145 becomes zero. On the other hand, when hydrogen is present it combusts at the catalyst 131*b* of the gas detection element 131. As a result, the temperature of the coil 131*a* becomes higher and the resistance value R14 increases. Since hydrogen does not combust at the temperature compensation element 132, the resistance value R13 does not change. Thereby, the balance of the bridge circuit is lost and a voltage which increases in accordance with the concentration of hydrogen is applied to the detection circuit 145. The voltage value is output from the detection circuit 145 to the output circuit 146 and the output circuit 146 outputs the voltage value to the control device 2. The concentration of hydrogen is computed in the control device 2 based on the map thereof which is predetermined in accordance with the voltage value.

A heater voltage generating circuit 147 which applies suitable voltage to the tube main portion 126*a* and the base flange portion 128*a* formed by the ceramic heater is connected to the outer power supply 143 to which the reference voltage generation circuit 144 is connected.

The control device 2 is connected to the sensor (not illustrated) and the tube main portion 126*a* and the base flange portion 128*a*, which are formed by the ceramic heater, in the gas detection chamber 127 and controls powering conditions of the gas detection element 131 and the temperature compensation element 132, and the tube main portion 126*a* and the base flange portion 128*a* for example, timing of start and stop of power distribution and amount thereof, in accordance with conditions of temperature and humidity of the ambient gas in the gas detection chamber 127 output from the sensor, conditions of loading and operation of the fuel cell 5 or the like. At this time, the control device 2 controls the amount of power distribution to the tube main portion 126*a* and the base flange portion 128*a* by feedback control in accordance with the current values distributed to the tube main portion 126*a* and the base flange portion 128*a* and chopper control (that is, switching on and off of the power distribution) based on on/off operations of a switching element, or the like.

For example, the control device 2 controls the power distribution to the tube main portion 126*a* and the base flange portion 128*a* based on the temperature measured by the sensor so that the temperature of the gas detection chamber 127 is within a predetermined range which is at least more than the dew-point temperature. The control device 2 also controls the timing of start and stop of power distribution and amounts thereof to the tube main portion 126*a* and the base flange portion 128*a* so that the relative humidity of the gas detection chamber 127 which is measured by the sensor becomes identical to an index value listed in the predetermined relative humidity map in accordance with the temperature of the gas detection chamber 127.

Furthermore, the control device 2 controls amounts of power distribution to the tube main portion 126*a* and the base flange portion 128*a* in accordance with various parameters such as operating conditions of the fuel cell 5 (including start and stop), conditions of the loading of the fuel cell 5 during operation such as a command to generate electricity sent to the fuel cell 5 (FC output command value), a current value of the fuel cell 5 measured by an output current sensor (not illustrated), and power generating conditions of the fuel cell 5 calculated based on a flow volume of the air supplied from an air compressor (not illustrated) to the fuel cell 5 measured by a flow volume sensor (not illustrated).

When loading of the fuel cell 5 becomes higher and there is a risk of the temperature inside the gas detection chamber 127 of the gas sensor 101 lowering due to an increase of the offgas which flows through the outlet pipe 9 of the oxygen electrode and cools the gas sensor 101, or of the relative humidity inside the gas detection chamber 127 increasing due to an increase of the produced water which is generated in the fuel cell 5 and included in the offgas, the control device 2 prevents condensation in the gas detection chamber 127 by raising the temperature inside the gas detection chamber 127. On the other hand, the control device 2 reduces energy consumption by lowering amounts of power distribution to the tube main portion 126*a* and the base flange portion 128*a* when loading of the fuel cell 5 becomes lower.

In addition, when a purge is conducted to drain water left in the fuel cell system due to an increase of the offgas flowing through the outlet pipes 8 and 9 when stopping operation of the fuel cell 5, the control device 2 increases the volume of the saturated water vapor of the ambient gas in the gas detection chamber 127 by raising the temperature of the gas detection chamber 127 by increasing power distribution to the tube main portion 126*a* and the base flange portion 128*a*. Thereby, condensation in the gas detection chamber 127 is prevented.

The control device 2 starts power distribution to the gas detection element 131, the temperature compensation element 132, the tube main portion 126*a*, and the base flange portion 128*a* before starting offgas flow in the outlet pipe 9 of the oxygen electrode when starting the fuel cell 5, and stops power distribution to the gas detection element 131, the temperature compensation element 132, the tube main portion 126*a*, and the base flange portion 128*a* after stopping offgas flow in the outlet pipe 9 of the oxygen electrode when stopping the fuel cell 5.

Functions of the gas sensor 101 of the aforementioned embodiment are described. The dehumidifier 137 provided in the gas detection chamber 127 absorbs and releases water in accordance with the humidity of the ambient gas in the gas detection chamber 127. For example, relative humidity in the gas detection chamber 127 decreases when power is distributed to the tube main portion 126*a* and the base flange portion 128*a* during operation of the gas sensor 101, due to the rise of the temperature inside the gas detection chamber 127. Thereby, the dehumidifier 137 releases water, and thus, more water can be absorbed therein. When the power distribution to the tube main portion 126*a* and the base flange portion 128*a* is stopped after offgas flow in the outlet pipe 9 is stopped when the fuel cell 5 is stopped, the relative humidity in the gas detection chamber 127 increases due to the decline of the temperature inside the gas detection chamber 127. At this time, the dehumidifier 137 absorbs water including water vapor in the ambient gas in the gas detection chamber 127 in accordance with its capacity.

Thereby, conditions in which condensation occurs such as the relative humidity in the gas detection chamber 127 becoming 100% and the temperature of the gas detection chamber 127 becoming equal to or less than the dew-point temperature can be prevented from occurring. In addition, even if condensation occurs when a temperature of a portion of the gas detection chamber 127 becomes equal to or less than the dew-point temperature, the water generated by condensation can be absorbed by the dehumidifier 137.

The dehumidifier 137 provided nearer the gas introduction portion 127a than the tube main portion 126a formed by the ceramic heater, between the gas detection element 131 and the temperature compensation element 132, and the gas introduction portion 127a can decrease the relative humidity of the ambient gas, to which the gas detection element 131 and the temperature compensation element 132 are exposed, and prevent condensation on the surfaces of the gas detection element 131 and the temperature compensation element 132.

Furthermore, since the inner wall of the gas detection chamber 127 is delimited by the tube main portion 126a formed by the ceramic heater, condensation on the inner wall of the gas detection chamber 127 can be prevented compared with the case where the tube portion 126 is formed by a metal or the like which has relatively higher heat conductivity.

As described above, the gas sensor 101 of the present embodiment can set a desired temperature and humidity in the gas detection chamber 127, maintaining uniformity of temperature and humidity distribution of the ambient gas in the gas detection chamber 127 and temperature distribution on the surfaces of the gas detection element 131 and the temperature compensation element 132, and prevent condensation caused by nonuniformity of temperature and humidity in the gas detection chamber 127.

In addition, since there is no need to provide an additional heater in the gas detection chamber 127, and the sintered filter 139 and the water-repellent filter 140 are provided in the outer case 138, the inner space of the gas detection chamber 127 can be made larger while preventing enlargement of the gas sensor 101 itself. This leads to preventing rapid change of the temperature and humidity in the inner space, and rapid decline of the temperatures of the ambient gas, the gas detection element 131, and the temperature compensation element 132 to below the dew-point temperature. Detection accuracy is also improved because the amount of the observed gas introduced in the gas detection chamber 127 increases.

Furthermore, since the dehumidifier 137 which absorbs water including water vapor in the ambient gas in the gas detection chamber 127 contacts the tube main portion 126a of the ceramic heater, the temperature of the dehumidifier 137 can be directly controlled by the ceramic heater. Therefore, for example, when offgas of high relative humidity brings water into the gas detection chamber 127, water adhesion on the surfaces of the gas detection element 131 and the temperature compensation element 132 and condensation in the gas detection chamber 127 can be prevented by rapidly heating and drying the dehumidifier 137 and controlling the absorbing capacity thereof.

Figure 11:
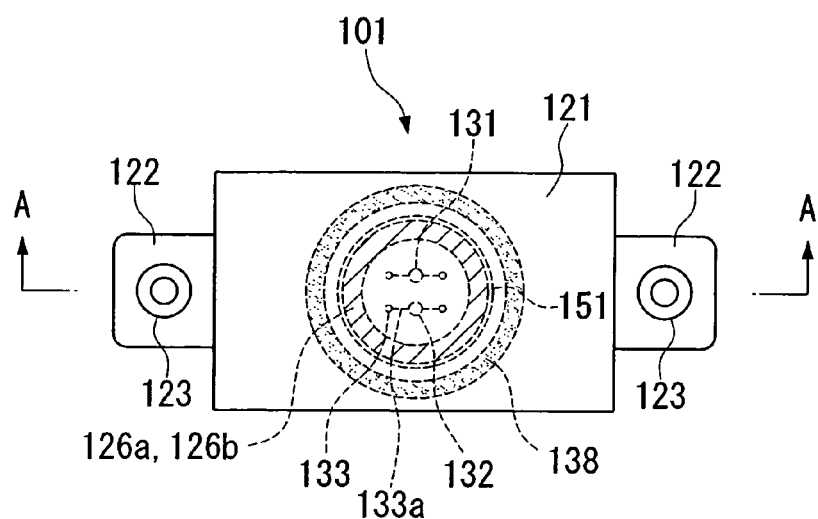
FIG. 11 is a sectional view of a gas sensor according to a variation of an embodiment of the present invention.
Figure 12:
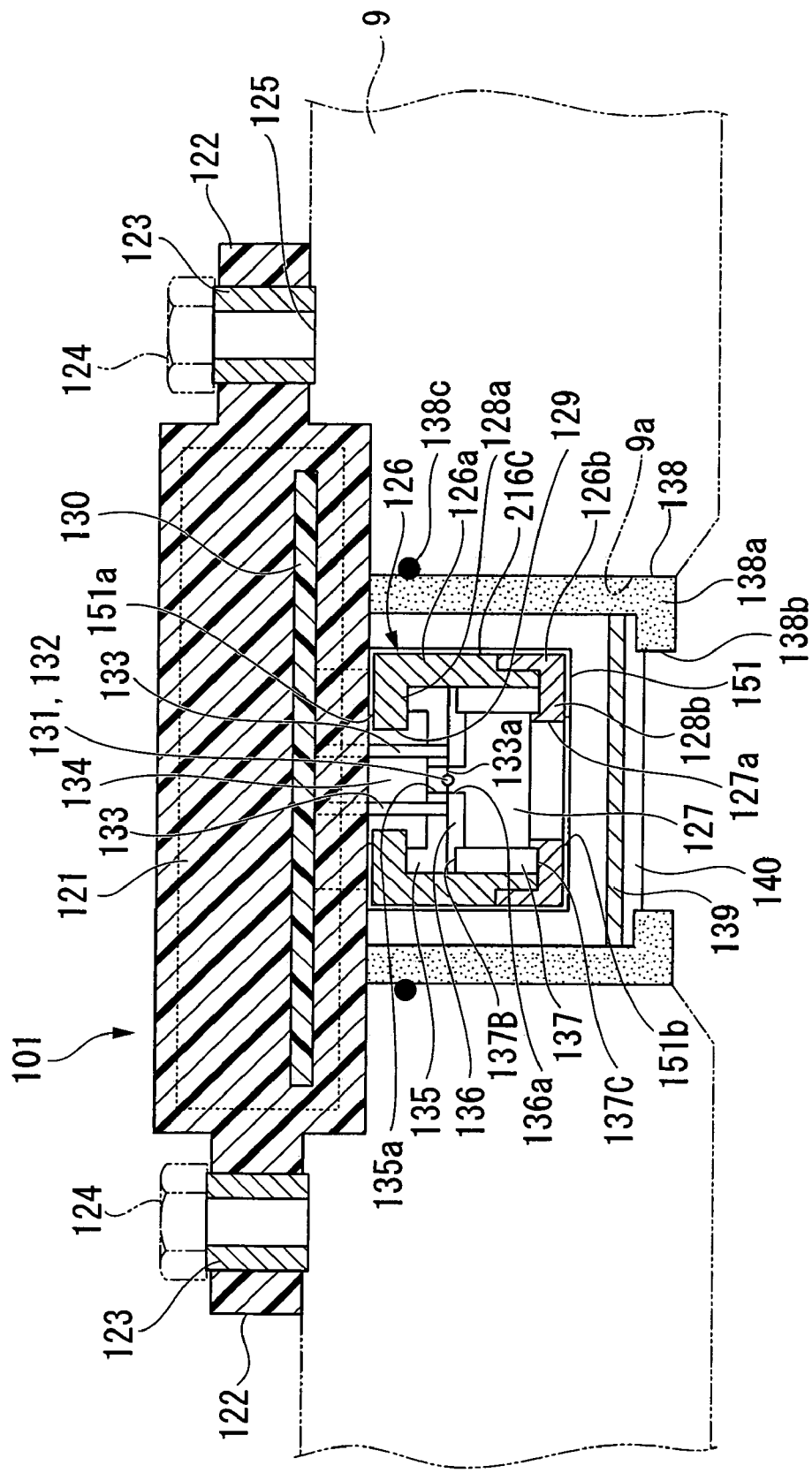
FIG. 12 is a schematic sectional view along line A-A of FIG. 11.
Figure 13:
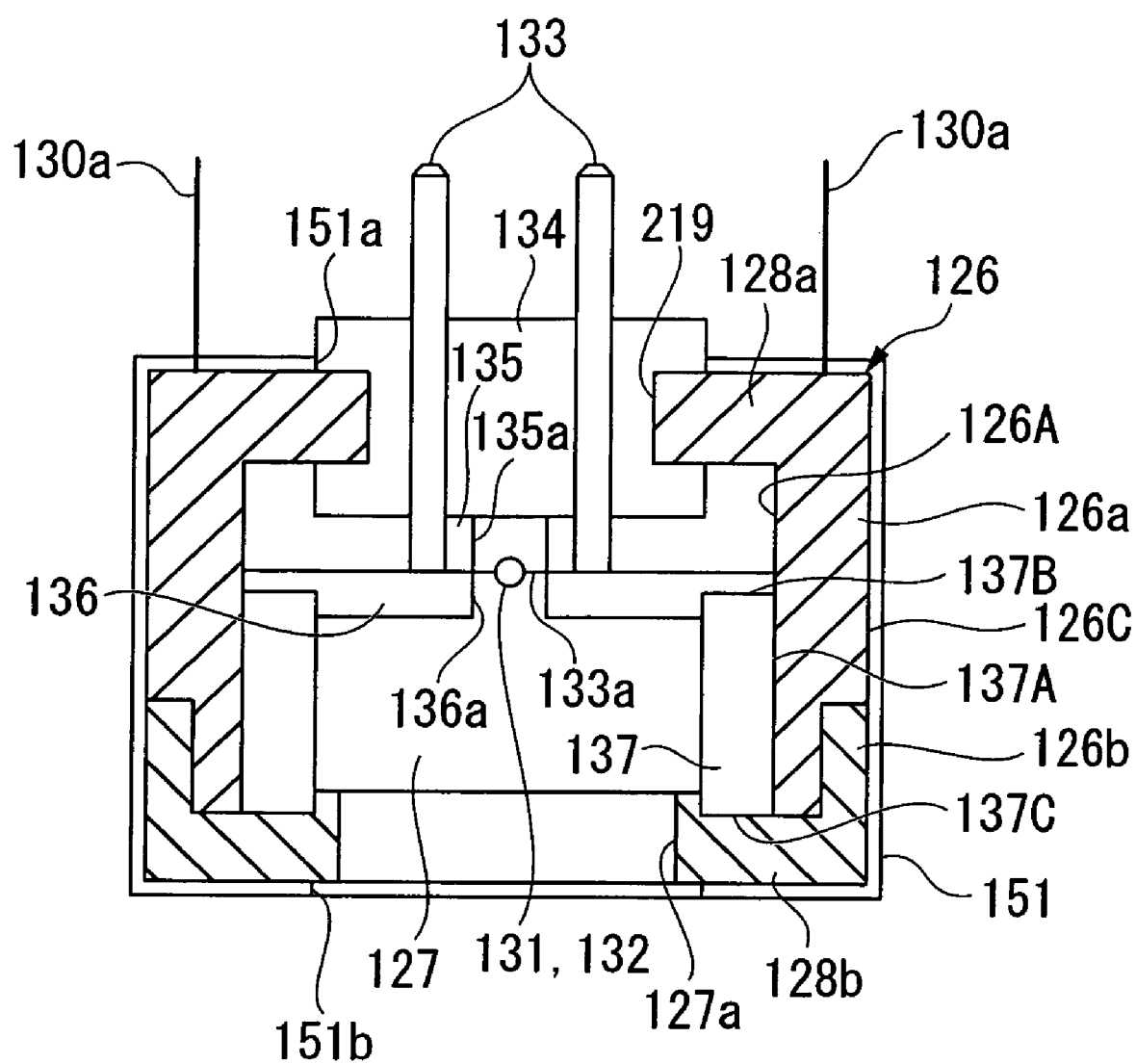
FIG. 13 is a detailed sectional view of the gas detection chamber shown in FIG. 12.

In the above embodiment, a heat insulating cover 151 made of heat insulating material may cover the outside of the tube portion 126 like a variation shown in FIGS. 11 to 13. In the heat insulating cover 151, apertures 151a and 151b are provided to communicate with the stay providing portion 129 of the tube portion 126 and the gas introduction portion 127a.

According to the variation, rapid change of the temperature in the gas detection chamber 127 and rapid decline of the temperatures of the ambient gas, the gas detection element 131, and the temperature compensation element 132 to below the dew-point temperature can be prevented.

Although the gas sensor 101 is a hydrogen sensor in the aforementioned embodiment, the gas sensor of the present invention is not limited thereto. The gas sensor may be one which measures other gases such as combustible gas of carbon monoxide and methane or the like.

In addition, although the gas sensor 101 is a catalytic combustion sensor in the aforementioned embodiment, the gas sensor of the present invention is not limited thereto. The gas sensor may be of another type such as a semiconductor type.

Furthermore, although the bridge circuit to which the gas detection element 131 and the temperature compensation element 132 are connected is provided in the gas sensor 101 of the aforementioned embodiment, the circuit is not limited thereto. The circuit may be of another type such as a series circuit and values of voltage or current between predetermined connecting points may be output to the control device 2 as parameters related to the resistance value R14 of the gas detection element 131.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A gas sensor comprising:
    walls delimiting a gas detection chamber, and having an introduction port through which an observed gas is introduced into the gas detection chamber;
    a measuring element disposed in the gas detection chamber, and measuring concentration of a subject gas contained in the observed gas;
    a heater constituting at least a portion of the walls, the portion facing the gas detection chamber; and
    a first dehumidifier absorbing water in a reversible manner, and disposed on a portion of the walls that is located opposite the introduction port with respect to the measuring element,
    wherein the heater includes a first heater which is tube-shaped and a second heater which is ring-shaped,
    and wherein the first dehumidifier is provided to be sandwiched between the first heater and the second heater.

2. A gas sensor according to claim 1, further comprising:
    a second dehumidifier absorbing water in a reversible manner, and disposed between the measuring element and the introduction port.

3. A gas sensor according to claim 2, wherein the heater is provided to be sandwiched between the first dehumidifier and the second dehumidifier.

* * * * *